United States Patent [19]

Alvarez

[11] 4,170,993
[45] Oct. 16, 1979

[54] SLIDING I.V. NEEDLE CARRIER ASSEMBLY

[76] Inventor: Marcial Alvarez, 225 E. Jersey St., Elizabeth, N.J. 07206

[21] Appl. No.: 885,553

[22] Filed: Mar. 13, 1978

[51] Int. Cl.$^2$ ............................................. A61M 05/00
[52] U.S. Cl. .............................. 128/214 R; 128/133; 128/321; 128/DIG. 26
[58] Field of Search ................ 128/214 R, 214.2, 215, 128/221, 133, DIG. 26

[56] References Cited

U.S. PATENT DOCUMENTS

| | | | |
|---|---|---|---|
| 2,409,432 | 10/1946 | Hubbard | 128/133 |
| 2,627,270 | 2/1953 | Glass | 128/218 A |
| 2,725,058 | 11/1955 | Rathkey | 128/221 |
| 2,876,770 | 3/1959 | White | 128/215 |
| 3,046,984 | 7/1962 | Eby | 128/214 R |
| 3,134,380 | 5/1964 | Armao | 128/215 |
| 3,463,152 | 8/1969 | Sorenson | 128/214.4 |
| 3,595,230 | 7/1971 | Suyeoka | 128/214.4 |

FOREIGN PATENT DOCUMENTS

| | | | |
|---|---|---|---|
| 1373027 | 8/1964 | France | 128/214.2 |
| 624269 | 6/1949 | United Kingdom | 128/214.4 |

*Primary Examiner*—Dalton L. Truluck
*Attorney, Agent, or Firm*—Weingram & Klauber

[57] ABSTRACT

An I.V. needle carrier assembly is disclosed which includes a delta-shaped base plate and an I.V. needle carrier-receiving barrel secured to the base plate and extending along the axis of symmetry thereof, so that the forward open end of the barrel resides at the apex of the delta. An I.V. needle carrier is slidingly received within the barrel and means are provided for sliding the carrier between a rearward position at which the needle tip is axially retracted within the barrel, and a forward position at which the needle tip is fully extended through the barrel front open end, whereby the needle may be inserted into the blood vessel of a patient. Adhesion means are affixed to the upper surfaces of the base plate at alternate sides of the barrel. These means include portions extendable beyond the lateral perimeter of the delta for anchoring the plate to the skin of the patient upon the needle being received into the blood vessel. The barrel includes a longitudinally extending slot through its surface and a pair of detents intersecting the slot. The needle carrier includes a grasping projection extending from the carrier and through the barrel slot to enable grasping by the user of the assembly during emplacement of the same. Axial movement of the grasping portion enables the user to displace the needle carrier between its rearward and forward positions, and the grasping portion may be rotated into the detents to lock the needle carrier at its rearward or forward position.

7 Claims, 4 Drawing Figures

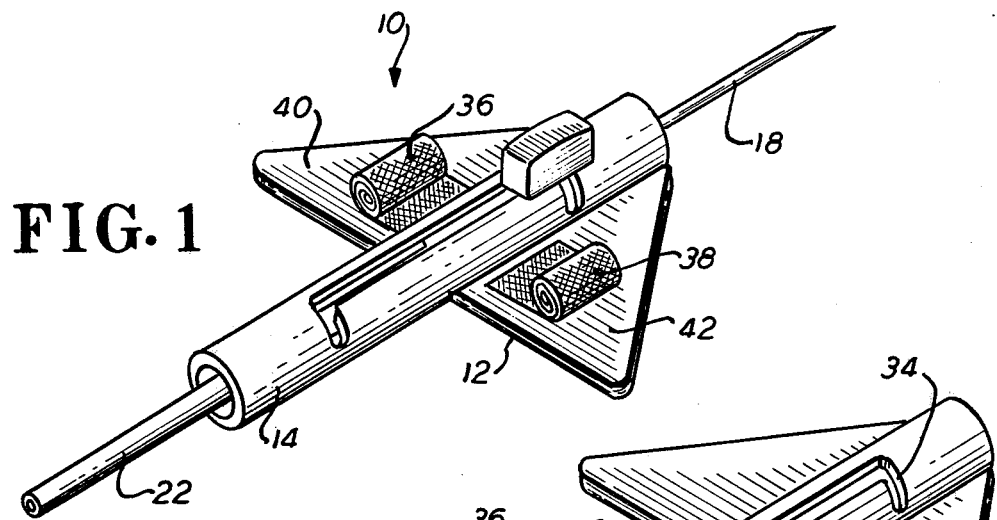
FIG. 1
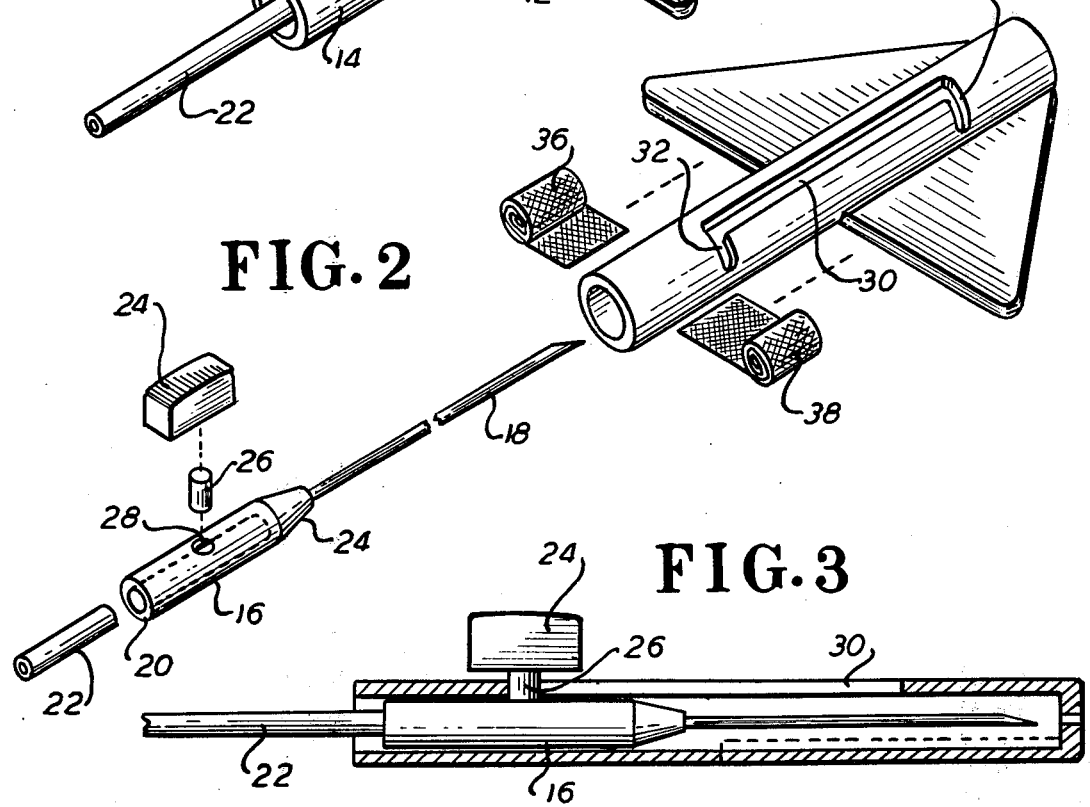
FIG. 2
FIG. 3
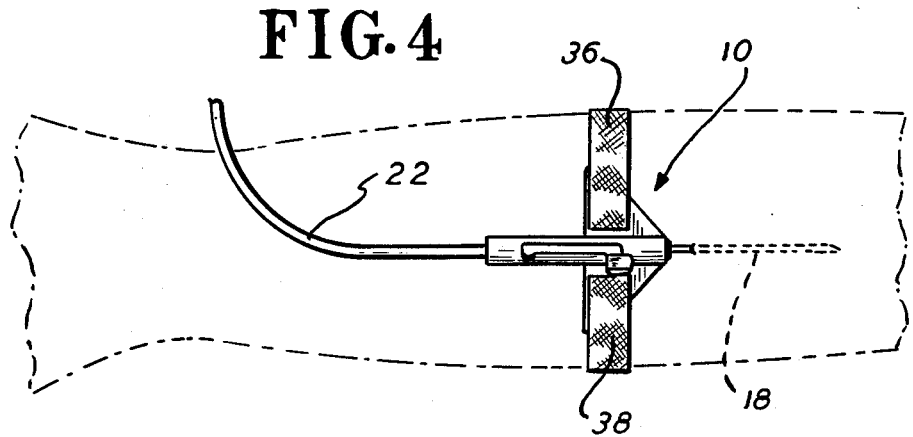
FIG. 4

SLIDING I.V. NEEDLE CARRIER ASSEMBLY

BACKGROUND OF INVENTION

This application is a continuation-in-part of my co-pending application, Ser. No. 744,406, filed Nov. 23, 1976, and entitled SLIDING I.V. NEEDLE CARRIER.

This invention relates generally to medical and surgical apparatus, and more specifically relates to an assembly useful in emplacing intravenous needles in the blood vessel of a patient to be thereby treated, and in retaining the emplaced needle.

Various techniques and apparatus have been utilized in the medical and surgical professions for the purposes of engaging intravenous needles or the like within blood vessels of patients to be treated by such devices, and for assuring that the said needles remain properly emplaced once so engaged. A common technique, for example, involves a simple emplacement of such an intravenous needle by the physician or medical attendant by direct grasping and manipulation of the usually cylindrical body carrying the needle. Once the needle is appropriately engaged, adhesive tape is then cut into strips and applied over the needle and associated tubing and adhered to the patient. This sort of approach, however, has been far from satisfactory. Aside from the difficulty of properly emplacing the needle by the technique mentioned, it may be noted that the emplaced needle is not fully stabilized by such arrangement, and can often become displaced from the vein. This in turn can create discomfort—or more serious problems for the patient.

In accordance with the foregoing, it may be regarded as an object of the present invention, to provide an I.V. needle carrier assembly which is so configured as to facilitate the user's manipulation of same, and thereby to facilitate accurate positioning and emplacing of the needle in a patient's blood vessel, thereby avoiding improper emplacement or injury or repeated puncturing of the patient's skin and blood vessels.

It is a further object of the present invention, to provide apparatus of the foregoing character, wherein the needle proper prior to use is fully retracted within a protective encasement, thereby protecting the needle from damage and encouraging a sterile condition for same.

It is a further object of the invention, to provide apparatus of the foregoing character, which includes simply operated means for affixing the assembly to the skin of the patient following needle emplacement thereby assuring that the needle will remain properly positioned.

SUMMARY OF INVENTION

Now in accordance with the present invention, the foregoing objects, and others as will become apparent in the course of the ensuing specification, are achieved in an I.V. needle carrier assembly which includes a delta-shaped base plate together with an I.V. needle carrier-receiving barrel which is secured to the base plate and extends along the axis of symmetry thereof, so that the forward open end of the said barrel resides at the apex of the delta.

An I.V. needle carrier is slidingly received in the barrel, and means are provided for sliding the needle carrier between the first or the rearward position at which the needle tip is axially retracted within the barrel, and a second or forward position at which the needle tip is fully extended through the barrel open end, in which position the needle may be inserted into the blood vessel of the patient.

Adhesion means are affixed to the surfaces of the base plate to alternate sides of the barrel. These means include portions extendable beyond the lateral perimeter of the delta, which enables anchoring of the plate to the skin of the patient upon the needle being received into the blood vessel.

The barrel includes a longitudinally extending slot through its surface, and a pair of detents intersecting the slot. The needle carrier includes a grasping projection which extends from the carrier and through the barrel slot to enable grasping and manipulation by the user of the assembly during emplacement of same. Axial movement of the grasping portion further enables the user to displace the needle carrier between its rearward and forward positions, and the grasping portion may be rotated into the detents to lock the needle carrier at its rearward or forward position.

During emplacement of the assembly by the user, the then upwardly facing grasping means are held by the user between thumb and forefinger. The wing-like portions of the delta-shaped base plate then constrain and-/or bear against the portions of the hand to alternate sides of the grasping portion, in consequence of which a very stable configuration is enabled, which tends to prevent the rotation or oscillation of the grasped assembly during the manipulative efforts involved in emplacing the needle point in the blood vessel.

Once the device is thus emplaced, the user may rotate the grasping portion to lock the needle in its forward position, and the user may thereupon activate the affixation means to retain the assembly in place.

The affixation means preferably comprise a pair of adhesive strips which are rolled onto themselves to define initially coiled cylinders at the upper surface of the base plate to alternate sides of the barrel. These strips are simply uncoiled until the ends thereof extend beyond the lateral perimeter of the delta, and then pressed to the skin surfaces to retain the entire assembly in place.

BRIEF DESCRIPTION OF DRAWINGS

The invention is diagrammatically illustrated, by way of example, in the drawings appended hereto, in which:

FIG. 1 is a perspective view of a needle carrier assembly in accordance with the present invention;

FIG. 2 is a perspective view similar to FIG. 1, but showing the component elements thereof in exploded fashion;

FIG. 3 is a longitudinal cross-sectional view through the apparatus of FIG. 1, depicting the needle carrier in its rearward retracted position, with the carrier being unlocked however; and FIG. 4 is a simplified schematic view similar to FIG. 1, but illustrating the assembly of FIG. 1 in an emplaced condition with respect to a patient.

DESCRIPTION OF PREFERRED EMBODIMENT

In FIGS. 1 and 2 herein, a needle carrier assembly 10 in accordance with the present invention is illustrated. Assembly 10 is seen to consist generally of a delta-shaped base plate 12, an I.V. needle carrier-receiving barrel 14 which is secured to base plate 12 along its axis of symmetry, and an I.V. needle carrier 16 (FIG. 2), which is slidingly received within barrel 14 and which carries at its forward end a conventional I.V. needle 18.

Base plate 12 and barrel 14 may comprise separate pieces, or depending upon the choice of materials, can be fabricated as a unit. For example the two mentioned components may be molded as a unit of a plastic material such as polyethylene or of other plastic which is acceptable for medical apparatus purposes. The components thus far discussed can also be formed of other durable materials, including, e.g., metal such as stainless steel, aluminum or the like. If the said components indeed comprise a suitable, durable material, they may be subjected to re-use and sterilization; in many instances, however, it is contemplated that the entire assembly 10 is to be packaged in a sterile container intended for one-time use, i.e., the entire assembly 10 may be of suitable plastics and be completely disposable after use.

The needle carrier 16 is seen to comprise generally a hollow cylinder, the rearward end 20 of which is engaged by a piece of standard tubing 22 of plastic or the like, which tubing may carry the usual solutions to be fed to the patient once needle 18 is properly engaged. The needle 18 is seen further to engage with cylinder 16 at the forward tapered end 25 thereof.

It is further seen that a grasping portion 24, comprising an enlarged knob is engaged with the needle carrier 16 via connecting stud 26 which passes into the grasping portion 24 and into an opening 28 at the side of the cylinder. The stud 26 of course engages barrel 16 in fluid-tight relationship therewith, so that no leakage of the fed solutions can occur.

Barrel 14 is seen to be provided with a longitudinally extending slot 30, which as is seen further in FIG. 3 passes through the wall of the barrel. When carrier 16 is received within barrel 14 the connecting stud 26 passes through this slot 30 so that the grasping portion 24 resides outside barrel 14, where it may be readily grasped and manipulated by a user.

It is further seen that a pair of detents, including a rearward detent 32 and a forward detent 34, again defined by slots passing through the wall of barrel 14, extend at right angles to slot 30 at the rearward and forward ends of the slot. Thus it will be evident that the user may, by grasping portion 24 displace in a forward or rearward direction the entire carrier 16, and further that once the fully rearward or forward position is achieved, the user by rotating the grasping portion 24 may displace stud 26 into detents 32 or 34 to thereby lock the needle carrier at its rearward or forward position.

The assembly 10 is further provided with affixation means, which comprise a pair of adhesive strips 36 and 38. These strips are provided on their lower surface with an adhesive material, such as a pressure sensitive adhesive composition. As seen in FIG. 1, the device prior to emplacement includes the adhesive strips in a configuration wherein the strips are rolled onto themselves to thereby initially present coils or rolled cylinders on alternate sides of barrel 14, i.e., rolled cylinders on the alternate wing-like portions 40 and 42 of the delta-shaped plate 12.

With the aid of the foregoing, operation of the present device may now be fully comprehended. Thus it will be clear that initially, the entire assembly 10 may be stored or packaged with the needle fully withdrawn, i.e., with needle carrier 16 in its rearward position and with the grasping portion 24 locked at the rearward detent 32. In this configuration, as may be appreciated, e.g., from FIG. 3, the needle is fully withdrawn within barrel 14, and thus protected against damage and its sterile condition maintained. At the same time, the unit in its initial configuration includes the adhesive strips 36 and 38 in their fully coiled position as shown in FIG. 1.

The user then manipulates the grasping portion 24 to achieve the configuration shown in FIG. 1. At this point the unit is ready for emplacement and the user continues to grasp the portion 24—typically utilizing the thumb and forefinger. During this operation, the wing-like portions 40 and 42 projecting to alternate sides of the portion 24 grasped, tend to constrain any rotational movement of the hand with respect to the axis of the assembly. Thus the user finds that the unit is stably grasped, whereupon he may proceed to accurately move the device forward and accurately insert it into the blood vessel of the patient.

At this point with the needle inserted, the user slightly lowers the assembly to bring the lower surface of plate 12 into contact with the patient's skin, and as best seen in the schematic view of FIG. 4, the coiled strips 36 and 38 are rapidly unrolled and affixed to the patient's skin to completely and securely emplace the assembly. At the same time, or immediately subsequent thereto, the grasping portion 24 is slightly rotated so as to lock it into detent 34, and thereby lock the needle in its forward, now emplaced position.

While the present invention has been described in terms of specific embodiments thereof, it will be understood in view of the instant disclosure, that numerous variations upon the invention are now enabled to those skilled in the art, which variations yet reside within the scope of the present teaching. Accordingly the invention is to broadly construed, and limited only by the scope and spirit of the claims now appended hereto.

I claim:

1. An I.V. needle carrier assembly, comprising in combination:

a delta-shaped base plate;

an I.V. needle carrier-receiving barrel being secured to said base plate, and extending along the axis of symmetry thereof, the forward open end of said barrel residing at the apex of said delta;

an I.V. needle carrier being slidingly received within said barrel, said carrier having a needle mounted thereon;

means for sliding said needle carrier between a rearward position at which the tip of said needle is axially retracted within said barrel, and a forward position at which said needle tip is fully extended through said front open end of said barrel, whereby said needle may be inserted into the blood vessel of a patient locking means for maintaining said carrier in at least the forward position; and adhesion means on the wing-like portions of said delta-shaped plate to alternate sides of said barrel, for anchoring said plate to the skin of said patient upon said needle being received into said blood vessel.

2. Apparatus in accordance with claim 1, wherein said barrel includes a longitudinally extending slot through the surface thereof, and a pair of detents intersecting said slot; and wherein said needle carrier includes a grasping means extending from said carrier and through said slot for grasping by the user of said assembly, longitudinal means of said grasping means enabling said user to move said needle carrier between said rearward and forward positions, and said grasping means being receivable into said forward or rearward detents, said means and needle thereby being locked into said rearward or forward positions.

3. Apparatus in accordance with claim 1, wherein said adhesion means is provided on the upper surface of said wing-like portions, and includes portions extendable beyond the lateral perimeter of said delta for adherence to said patient skin.

4. Apparatus in accordance with claim 3, wherein said adhesion means comprises a pair of adhesive strips rolled onto themselves at alternate sides of said barrel to define uncoilable cylinders, uncoiling of said cylinders upon emplacement of said needle extending portions of said strips beyond said delta lateral perimeter to enable adherence to said patient skin.

5. A device in accordance with claim 1, wherein substantially all portions of said assembly comprises a sterilizable plastic.

6. A device in accordance with claim 1, wherein said needle carrier includes a portion projecting through said barrel, said projecting portion being graspable by a user of said assembly to displace said carrier between said forward and rearward positions.

7. A device in accordance with claim 6, wherein said graspable portion is engagable with forward and rearward locking means on said barrel, for maintaining the retracted position of said needle carrier prior to use of said assembly, and for locking said needle carrier in its forward position during use of said assembly in conjunction with patient treatment.

* * * * *